(12) United States Patent
Hobbs et al.

(10) Patent No.: US 8,785,128 B2
(45) Date of Patent: Jul. 22, 2014

(54) GENETIC DIAGNOSIS OF HEPATIC STEATOSIS

(71) Applicants: Helen H Hobbs, Dallas, TX (US); Jonathan C Cohen, Dallas, TX (US)

(72) Inventors: Helen H Hobbs, Dallas, TX (US); Jonathan C Cohen, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/684,577

(22) Filed: Nov. 26, 2012

(65) Prior Publication Data

US 2014/0179536 A1 Jun. 26, 2014

Related U.S. Application Data

(63) Continuation of application No. 12/553,330, filed on Sep. 3, 2009, now abandoned.

(60) Provisional application No. 61/094,408, filed on Sep. 4, 2008.

(51) Int. Cl.
*C12Q 1/68* (2006.01)
*A61K 31/00* (2006.01)
*A61K 38/28* (2006.01)
*A61K 38/16* (2006.01)

(52) U.S. Cl.
CPC .................................. *C12Q 1/6883* (2013.01)
USPC .......... 435/6.11; 435/6.18; 536/23.5; 514/6.9; 514/7.1; 514/7.3; 514/7.4; 514/4.8

(58) Field of Classification Search
None
See application file for complete search history.

(56) References Cited

PUBLICATIONS

The Free Dictionary, definition for "determining", printed on Mar. 4, 2014, available via url: <.thefreedictionary.com/determining>.*
The Free Dictionary definition for "measuring", printed on Mar. 18, 2014, available via url: < thefreedictionary.com/measuring>.*
Johansson et al. Diabetes. Mar. 2006. 55(3): 826-833.*

* cited by examiner

*Primary Examiner* — Carla Myers
(74) *Attorney, Agent, or Firm* — Richard Aron Osman

(57) ABSTRACT

Disclosed are methods of identifying a genetic variant in a person determined to have or be predisposed having a fatty liver by determining whether the person has PNPLA3-I148M. Also disclosed are methods of identifying a genetic variant in a person by determining whether the person has PNPLA3-I148M; and prescribing to the person a treatment to reduce liver fat or associated inflammation.

20 Claims, No Drawings

GENETIC DIAGNOSIS OF HEPATIC STEATOSIS

This application is a continuation of Ser. No. 12/553,330, filed Sep. 3, 2009, which claims priority to U.S. Ser. No. 61/094,408, filed: Sep. 4, 2008.

The field of the invention is sequence variations in the human gene PNPLA3 as risk factors for hepatic steatosis and hepatic injury.

This work was supported by grants from the NIH and NHLBI Program for Genomic Applications (HL-066681); the Government has certain rights in this invention.

BACKGROUND OF THE INVENTION

Nonalcoholic fatty liver disease (NAFLD) is a burgeoning health problem of unknown etiology that varies in prevalence among ethnic groups. To identify genetic variants/polymorphisms contributing to differences in hepatic fat content, we performed a genome-wide association scan of nonsynonymous sequence variations in a multiethnic population. A variant (I148M) in PNPLA3 (Patatin-like phospholipase domain containing 3) was strongly associated with increased hepatic fat levels and with hepatic inflammation. The variant was most common in Hispanics, the group most susceptible to NAFLD; homozygotes had a >2-fold higher hepatic fat content. Resequencing revealed another variant associated with lower hepatic fat content in African-Americans, the group at lowest risk of NAFLD. Thus, variation in PNPLA3 contributes to ethnic and inter-individual differences in hepatic fat content and susceptibility to NAFLD.

SUMMARY OF THE INVENTION

In one embodiment, the invention provides methods and compositions for identifying a genetic variant in a person determined to have or be predisposed to having a liver disease, the method comprising the step of determining whether the person has PNPLA3-I148M.

In another embodiment, the invention provides methods and compositions for identifying a genetic variant in a person, the method comprising the steps of (a) determining whether the person has PNPLA3-I148M; and (b)(i) providing the person with information about risk of developing a liver disease, or (ii) providing the person with a recommendation for an additional diagnostic test or monitoring to detect an indication of the liver disease, or (iii) prescribing to the person a treatment for the liver disease.

In particular embodiments, the liver disease is fatty liver, an increase in or supra-normal hepatic fat, hepatic steatosis, steatohepatitis, nonalcoholic fatty liver disease, or associated inflammation.

In particular embodiments, the methods further comprise the step of determining whether the person has PNPLA3-S453I.

In particular embodiments, the determining step comprises detecting the PNPLA3-I148M and/or PNPLA3-S453I using a method selected from the group consisting of: mass spectroscopy, oligonucleotide microarray analysis, allele-specific hybridization, allele-specific PCR, and sequencing.

In particular embodiments, the determining step comprises detecting a marker of PNPLA3-1148M that is SNP rs738409, or a surrogate SNP in linkage disequilibrium with the PNPLA3-1148M and having a $r^2$ value greater than 0.5.

As described further below, the variant allele PNPLA3-1148M is readily detected by associated SNPs that are in linkage disequilibrium with PNPLA3-1148M, and provide markers for this allele: SNP markers for PNPLA3-1148M include rs738409 ($r^2$=1) and associated SNPs having a $r^2$ value greater than 0.5. In Table 1 below, the rs number is shown, followed by the correlation with the 1148M allele ($r^2$ value). These data are from Caucasians in the HapMap.

TABLE 1

| SNP markers for I148M | | | |
|---|---|---|---|
| rs12483959 | 0.657 | rs2072905 | 0.609 |
| rs11090617 | 0.624 | rs2896019 | 0.607 |
| rs4823173 | 0.598 | rs2073081 | 0.568 |
| rs2076211 | 0.657 | rs1010023 | 0.609 |
| rs1977081 | 0.609 | rs1010022 | 0.609 |
| rs1883349 | 0.643 | rs926633 | 0.609 |
| rs2281135 | 0.609 | rs2294916 | 0.609 |
| rs2072907 | 0.609 | rs4823179 | 0.579 |

In particular embodiments, the determining step comprises detecting a plurality of the SNP and surrogate SNP markers.

In particular embodiments, the methods further comprise an antecedent step of determining that the person has or is predisposed to having a subject liver disease. The subject liver diseases are amenable to convention clinical diagnosis; for example, fatty liver or hepatic steatosis may be determined inter alia using computer-aided tomography (CAT) scan or NMR, such as proton magnetic resonance spectroscopy, and is generally clinically defined as hepatic triglyceride greater than 5.5%. Indicators of predisposition to fatty liver include obesity, diabetes, insulin resistance, and alcohol ingestion.

In particular embodiments, the methods may further comprise the step of prescribing to the person a treatment for the liver disease or treating the person with a therapy for the liver disease, such an anti-obesity drug such as Orlistat, Sibutramine, Byetta, Symlin, Rimonabant, or an anti-diabetic drugs such as a thiazolidinedione (e.g. rosiglitazone), or metformin or glimepiride, or anti-inflammatory drugs.

In another embodiment, the invention provides methods and compositions for identifying a genetic variant in a person determined to have or be predisposed to having a subnormal hepatic fat or triglyceride content, or a subnormal susceptibility to hepatic steatosis or nonalcoholic fatty liver disease, the method comprising the step of determining whether the person has PNPLA3-S453I.

In another embodiment, the invention provides methods and compositions for identifying a genetic variant in a person, the method comprising the steps of: (a) determining whether the person has PNPLA3-S453I; and (b) providing the person with information about predisposition to have a subnormal hepatic fat or triglyceride content or a subnormal susceptibility to hepatic steatosis or nonalcoholic fatty liver disease, or providing the person with a recommendation for an additional diagnostic test or monitoring to detect an indication of liver disease, or prescribing to the person an alternative treatment for liver disease.

In particular embodiments, the determining step comprises detecting the variant using a method selected from the group consisting of: mass spectroscopy, oligonucleotide microarray analysis, allele-specific hybridization, allele-specific PCR, and sequencing.

In particular embodiments, the determining step comprises detecting a marker of PNPLA3-S453I that is SNP rs6006460, or a surrogate SNP in linkage disequilibrium with the PNPLA3-S453I and having a $r^2$ value greater than 0.5.

In particular embodiments, the determining step comprises detecting a plurality of the SNP and surrogate SNP markers.

DETAILED DESCRIPTION OF SPECIFIC EMBODIMENTS OF THE INVENTION

In other embodiments, the invention provides reagents and kits for practicing the disclosed methods.

Genetic variation in PNPLA3 confers susceptibility to fatty liver disease. In humans, adipose tissue serves as a reservoir to limit the deposition of triglyceride (TG) in the liver and other metabolically active tissues[1]. The effectiveness of this buffer in protecting against the accumulation of fat in the liver varies widely among individuals: hepatic fat content ranges from less than 1% to more than 50% of liver weight in the general population[2]. The accumulation of excess TG in the liver, a condition known as hepatic steatosis (or fatty liver), is associated with adverse metabolic consequences, including insulin resistance and dyslipidemia[3,4]. In a subset of individuals hepatic steatosis promotes an inflammatory response in the liver, referred to as steatohepatitis, which can progress to cirrhosis and liver cancer[3,5]. Nonalcoholic fatty liver disease (NAFLD) is the most common form of liver disease in Western countries[6]. Approximately 10% of liver transplants performed in the United States are for cirrhosis related to NAFLD[4].

Factors promoting deposition of fat in the liver include obesity, diabetes, insulin resistance, and alcohol ingestion[3,6]. Hispanics are particularly susceptible to develop fatty liver and also have a higher prevalence of steatohepatitis and cirrhosis, whereas African-Americans tend to be resistant to the accumulation of liver fat and are less prone to develop liver failure[2,7-9].

To identify DNA sequence variations that contribute to inter-individual differences in NAFLD, we performed a genome-wide survey of nonsynonymous (NS) sequence variations in a multiethnic population-based study, the Dallas Heart Study[10], in which hepatic TG content was measured using proton magnetic resonance spectroscopy ($^1$H-MRS), the most accurate, quantitative noninvasive method available[2,11,12]. We assayed directly the sequence variations with a higher likelihood of affecting gene function. Of the 12,138 NS variants assayed using chip-based oligonucleotide hybridization[13], 9,229 exceeded the quality control threshold for the study (see METHODS) and were included in the analysis.

Each variant was tested for association with hepatic fat content in the 1,032 African-American, 696 European-American and 383 Hispanic study participants in the Dallas Heart Study who obtained $^1$H-MRS of the liver[2]. To maximize statistical power, the three ethnic groups were pooled and global ancestry was included as a covariate to control for population stratification (see METHODS). The quantile-quantile plot of P-values showed no systematic deviation from the null distribution.

A single variant in PNPLA3 (rs738409) was strongly associated with liver fat content ($P=5.9 \times 10^{-10}$). The variant is a cytosine to guanine substitution that changes codon 148 from isoleucine to methionine; this residue is highly conserved in vertebrates. PNPLA3 encodes a 481 amino acid protein of unknown function that belongs to the patatin-like phospholipase family[14]. The progenitor of this family, patatin, is a major protein of potato tubers and has nonspecific lipid acyl hydrolase activity[15,16]. None of the other NS sequence variants tested in the genome-wide scan exceeded the Bonferroni-corrected threshold for significance ($P=5.4 \times 10^{-6}$).

The association between PNPLA3-I148M and hepatic fat content remained highly significant ($P=7.0 \times 10^{-14}$) after adjusting for BMI, diabetes status, ethanol use, as well as global and local ancestry, and was associated with a significant increase in liver TG content in all three ethnic groups. Thus, the association between rs738409 and liver fat content was not attributable either to the effect of known risk factors for liver fat accumulation or to population stratification.

The frequencies of the PNPLA3-I148M allele mirrored the relative prevalence of NAFLD in the three ethnic groups[2]; the highest frequency was in Hispanics (0.49), with lower frequencies observed in European Americans (0.23) and African-Americans (0.17). Accordingly, we examined the relationship between PNPLA3-I148M and evidence of hepatic inflammation, as indicated by release of liver enzymes into the circulation. A significant elevation in serum levels of alanine aminotransferase (ALT) was found in association with the PNPLA3-I148M allele in the entire sample ($P=3.7 \times 10^{-4}$). Analysis of the three ethnic groups revealed that the association with ALT was limited to the Hispanics ($P=1.3 \times 10^{-5}$), the group with the greatest prevalence of hepatic steatosis and susceptibility to cirrhosis[2,7]. The PNPLA3-I148M allele was also associated with serum aspartate aminotransferase levels in Hispanics ($P=0.002$). These findings are consistent with our prior observation that a higher proportion of Hispanics with hepatic steatosis have evidence of associated inflammation, and indicates that PNPLA3-I148M allele adversely affects liver function.

Increased hepatic fat content is associated with insulin resistance and dyslipidemia (increased plasma levels of TG and lower levels of high density lipoprotein-cholesterol), but the causal nature of these relationships remains poorly defined[3]. No association was found between the PNPLA3-I148M allele and body mass index (BMI) or indices of insulin sensitivity, including fasting glucose and insulin or homeostatic model assessment of insulin resistance (HOMA-IR) in the Dallas Heart Study. No associations were observed between PNPLA3 genotype and plasma levels of TG, total cholesterol, HDL-cholesterol or LDL-cholesterol. A corresponding analysis in a larger, biracial sample (n=14,821), the Atherosclerosis Risk in Communities Study[17], also revealed no association of PNPLA3-I148M with BMI, indices of insulin sensitivity, or plasma levels of TG or HDL-C. The data from these studies indicate that the PNPLA3-I148M allele is associated with a systematic increase in liver fat content but not with major alterations in glucose homeostasis or lipoprotein metabolism. Thus, increased liver fat content does not inevitably lead to insulin resistance, which is consistent with recent observations in various animal models[18,19].

To determine if other sequence variations in PNPLA3 contribute to differences in hepatic fat content, we resequenced the coding region of PNPLA3 in the 80 men (32 African-Americans, 32 European-Americans, and 16 Hispanics) and 80 women who had the highest levels of liver fat in the Dallas Heart Study, and in a sex- and ethnicity-matched group with the lowest levels[2]. The number of individuals with NS variants found only in the high group (n=10) was similar to the number found only in the low group (n=8), but the three subjects with likely null mutations (Fs-Y21 and IVS7+1) were all in the high group, which is consistent with loss-of-function of PNPLA3 causing an increase in hepatic TG content.

Eight variants were present in both the low and the high hepatic fat groups and the six most common were genotyped in the sample. One variant, PNPLA3-S453I was common in African-Americans (MAF=0.104) but rare in European-Americans (0.003) and Hispanics (0.008). Median liver fat content was 18% lower in African-Americans with the PNPLA3-S453I allele when compared to African-Americans homozygous for the wild-type allele (3.3% versus 2.7%, P=6×10⁻⁴). Further evidence that the variant was associated with lower hepatic fat content was the finding that a significantly greater number of individuals with the PNPLA3-S453I allele were present in the individuals with a hepatic fat content in the lowest decile when compared to the highest decile of the population. No significant differences in the number of individuals identified in the extremes were found for any of the other five SNPs.

The identification of a second allele of PNPLA3 that was independently associated with liver fat content further supports a role for PNPLA3 in determining liver fat levels, and indicates the presence of both loss-of-function and gain-of-function alleles at this locus.

The frequencies of PNPLA3-I148M and of PNPLA3-S453I in the three ethnic groups represented in the Dallas Heart Study correlate with ethnic differences in the relative propensity to develop NAFLD (Hispanics>Caucasians>African-Americans)[2]. Exclusion of the individuals carrying either of these two alleles (PNPLA3-I148M and PNPLA3-S453I) attenuated the differences in liver fat content between the ethnic groups; regression analysis indicated that these two sequence variations accounted for 72% of the observed ethnic differences in hepatic fat content. Thus, genetic variation in PNPLA3 accounts for a large fraction of the ethnic differences in the propensity to accumulate excess fat in the liver.

Expression of PNPLA3 is under metabolic control in adipose tissue and the liver, with levels being low in the fasted state and increases dramatically with carbohydrate feeding[20, 21]. PNPLA3 structurally resembles calcium-independent phospholipase $A_2$ but the recombinant protein has low phospholipase activity when expressed in insect (Sf9) cells[22]. PNPLA3 has more robust activity against TG in vitro and can also transfer fatty acids to and from mono- and diacylglycerol[22].

Our finding that markers of liver inflammation (serum levels of liver-derived enzymes) were elevated in 148M carriers, indicates that genetic variation PNPLA3-I148M allele can confer susceptibility to disease progression. Patatin-like phospholipase family members in other organisms are up-regulated in response to environmental insults[23]. The sequence variations we have identified in PNPLA3 provides predictive information regarding the risk of developing hepatic steatosis and liver injury in response to environmental stresses such as caloric excess, infections, or drugs.

Methods; Study populations.

The Dallas Heart Study is a population-based probability sample of Dallas County. The sampling frame and the study design are described in detail in Victor et al.[10]. African-Americans were over-sampled (52% African American, self-identified as 'black', 29% European American, self-identified as 'white', 17% Hispanic self identified as "Hispanic" and 2% other ethnicities). The institutional review board of University of Texas Southwestern Medical Center approved the study. Alcohol consumption was determined according to answers to previously validated questions[2]. Blood pressure, height, weight and BMI and calculated variables were measured as described[10]. Fasting blood samples were obtained from 3,551 subjects (ages 30-65) and 2,971 of these individuals completed a clinic visit; hepatic TG content was measured using ¹H-MRS in 2,240 African-Americans, European-Americans and Hispanics[7,12].

The association between PNPLA3-I148M and metabolic phenotypes were also examined in the Atherosclerosis Risk in Communities Study (ARIC), a large prospective study that focuses on cardiovascular disease in European-Americans and African-Americans. Details of the ARIC study design and the methods used to measure plasma lipid levels have been published previously[17,24]. The data used in this analysis was collected from the baseline examination.

Whole-Genome Association and Other Statistical Methods.

A genome-wide association analysis was performed using 12,138 NS sequence variations from db SNP and the Perlegen SNP database. SNPs were assayed in 3,383 Africans-American, Caucasian and Hispanic participants of the Dallas Heart Study using high-density oligonucleotide arrays (Perlegen Sciences, Mountain View, Calif.). SNPs that met any of the following criteria were excluded (n=2,623): error probability>20%, genotype call rate<80%, or a significant deviation from Hardy-Weinberg Equilibrium (p-value <0.0001). Of the 9,515 SNPs that were successfully assayed, 286 were monomorphic in the Dallas Heart Study sample. The remaining 9,229 variants were tested for association with hepatic fat content in the 2,111 African-Americans, Caucasians and Hispanic subjects in the Dallas Heart Study who underwent ¹H-MRS of the liver[2] and in whom ancestry-informative SNPs had been assayed previously; global and local ancestries were inferred for each individual using STRUCTURE[25] with 2,270 ancestry-informative SNPs[26]. The results were almost identical when ancestry adjustment was performed with the same SNPs using principal components analysis. Though the ancestry-informative SNP panel was primarily designed for African-Americans [the mean multipoint information content[27] ($\overline{IC}$)=0.82], it was also adequately informative in European-Americans ($\overline{IC}$=0.63) and Hispanics ($\overline{IC}$=0.66). We pooled all participants together and inferred global ancestry setting the number of clusters K equal to 3.

The statistical significance of 9,229 SNPs in the whole genome association study was assessed using analysis of variance (ANOVA). To accommodate confounding factors, we included age, sex, and global ancestry as covariates in the model. The additive effect of each variant was tested by encoding the genotype variable as 0, 1, and 2. Since the distribution of hepatic TG levels is highly skewed, a power transformation ($\lambda$=¼) was applied to the trait before the analysis. To account for multiple testing, we adjusted the significance threshold for the number of tests performed using the Bonferroni method. SNPs with a nominal P-value <5.4×10⁻⁰⁶ were considered significant on a genome-wide scale.

The association between PNPLA3 variants and hepatic fat content within each ethnic group was tested using ANOVA, including age, gender, BMI, diabetes status, ethanol use and local ancestry as covariates. Individuals whose genetic ancestry was not consistent with their self-reported ancestry (n=11, 5, and 16 for African-Americans, European-Americans and Hispanics, respectively) and had a fractional ancestry was more than 3 times the inter-quartile range below the 25ᵗʰ percentile for their reference group were excluded from the analysis. Because the distribution of hepatic TG content is skewed, we reported medians and inter-quartile ranges.

The association of PNPLA3-I148M with BMI, HOMA-IR and plasma TG levels was analyzed in the African-Americans, Caucasians and Hispanics together using the ANOVA including age, gender, and local ancestry as covariates. HOMA-IR was adjusted for BMI and plasma TG levels were adjusted for BMI and diabetes.

To determined the contribution of PNPLA3 to the ethnic differences in liver fat content, we examined the proportion of variance explained by ancestry (R1) using a linear model. We then determined the proportion of variance explained by ancestry after adjusting for the PNPLA3 genotypes (148M and S453I) (R2). The proportion of variance due to ancestry and explained by 148M and S453I was determined from (R1−R2)/R1.

Resequencing PNPLA3.

The exons and flanking introns of PNPLA3 were sequenced as described previously[28] in the African-American, European-American and Hispanic men and women in the Dallas Heart Study with the highest and lowest hepatic TG content. All sequence variants identified were verified by manual inspection of the chromatograms and missense changes were confirmed by an independent resequencing reaction.

Genotyping Assays.

Fluorogenic 5'-nucleotidase assays were developed for PNPLA3-I148M and for the sequence variants identified in both the high and low hepatic TG groups in the resequencing experiments. Sequence variations in PNPLA3 were assayed using the TaqMan assay system (Applied Biosystems) on a 7900HT Fast Real-Time PCR instrument. Probes and reagents were purchased from Applied Biosystems.

REFERENCES

1. Wang, M. Y. et al. Adipogenic capacity and the susceptibility to type 2 diabetes and metabolic syndrome. *Proc Natl Acad Sci USA* 105, 6139-44 (2008).
2. Browning, J. D. et al. Prevalence of hepatic steatosis in an urban population in the United States: impact of ethnicity. *Hepatology* 40, 1387-95 (2004).
3. Browning, J. D. & Horton, J. D. Molecular mediators of hepatic steatosis and liver injury. *J Clin Invest* 114, 147-52 (2004).
4. McCullough, A. J. The clinical features, diagnosis and natural history of nonalcoholic fatty liver disease. *Clin Liver Dis* 8, 521-33, viii (2004).
5. Adams, L. A. et al. The natural history of nonalcoholic fatty liver disease: a population-based cohort study. *Gastroenterology* 129, 113-21 (2005).
6. de Alwis, N. M. & Day, C. P. Non-alcoholic fatty liver disease: the mist gradually clears. *J Hepatol* 48 Suppl 1, S 104-12 (2008).
7. Browning, J. D., Kumar, K. S., Saboorian, M. H. & Thiele, D. L. Ethnic differences in the prevalence of cryptogenic cirrhosis. *Am J Gastroenterol* 99, 292-8 (2004).
8. Clark, J. M., Brancati, F. L. & Diehl, A. M. The prevalence and etiology of elevated aminotransferase levels in the United States. *Am J Gastroenterol* 98, 960-7 (2003).
9. Caldwell, S. H., Harris, D. M., Patrie, J. T. & Hespenheide, E. E. Is NASH underdiagnosed among African Americans? *Am J Gastroenterol* 97, 1496-500 (2002).
10. Victor, R. G. et al. The Dallas Heart Study: a population-based probability sample for the multidisciplinary study of ethnic differences in cardiovascular health. *Am J Cardiol* 93, 1473-80 (2004).
11. Longo, R. et al. Proton MR spectroscopy in quantitative in vivo determination of fat content in human liver steatosis. *JMRI* 5, 281-285 (1995).
12. Szczepaniak, L. S. et al. Magnetic resonance spectroscopy to measure hepatic triglyceride content: prevalence of hepatic steatosis in the general population. *Am J Physiol Endocrinol Metab* 288, 462-468 (2004).
13. Hinds, D. A. et al. Whole-genome patterns of common DNA variation in three human populations. *Science* 307, 1072-9 (2005).
14. Wilson, P. A., Gardner, S. D., Lambie, N. M., Commans, S. A. & Crowther, D. J. Characterization of the human patatin-like phospholipase family. *J. Lipid Res.* 47, 1940-1948 (2006).
15. Rydel, T. J. et al. The crystal structure, mutagenesis, and activity studies reveal that patatin is a lipid acyl hydrolase with a ser-asp catalytic dyad. *Biochem* 42, 6696-6708 (2003).
16. Strickland, J. A., Orr, G. L. & Walsh, T. A. Inhibition of Diabrotica larval growth by patatin, the lipid acyl hydrolase from potato tubers. *Plant Physiol* 109, 667-674 (1995).
17. *ARIC manual of operations: No 2, cohort component procedures.*, (ARIC Coordinating Center, School of Public Health, University of North Carolina, Chapel Hill, 1987).
18. Minehira, K. et al. Blocking VLDL secretion causes hepatic steatosis but does not affect peripheral lipid stores or insulin sensitivity in mice. *J Lipid Res* (2008).
19. Monetti, M. et al. Dissociation of hepatic steatosis and insulin resistance in mice overexpressing DGAT in the liver. *Cell Metab* 6, 69-78 (2007).
20. Baulande, S., Lassnier, F., Lucas, M. & Pairault, J. Adiponutrin, a transmembrane protein corresponding to a novel dietary—and obesity-linked mRNA specifically expressed in the adipose lineage. *J Biol Chem* 276, 33336-33344 (2001).
21. Lake, A. C. et al. Expression, regulation, and triglyceride hydrolase activity of adiponutrin family members. *J Lipid Res* 46, 2477-2487 (2005).
22. Jenkins, C. M. et al. Identification, cloning, expression, and purification of three novel human calcium-independent phospholipase $A_2$ family members possessing triacylglycerol lipase and acylglycerol transacylase activities. *J Biol Chem* 279, 48968-48975 (2004).
23. Rietz, S., Holk, A. & Scherer, G. F. Expression of the patatin-related phospholipase A gene AtPLA IIA in Arabidopsis thaliana is up-regulated by salicylic acid, wounding, ethylene, and iron and phosphate deficiency. *Planta* 219, 743-53 (2004).
24. Brown, S. A. et al. Plasma lipid, lipoprotein cholesterol, and apoprotein distributions in selected U.S. communities. *Arteriscler. Thromb* 13, 1139-1158 (1993).
25. Falush, D., Stephens, M. & Pritchard, J. K. Inference of population structure using multilocus genotype data: linked loci and correlated allele frequencies. *Genetics* 164, 1567-87 (2003).
26. Smith, M. W. et al. A high-density admixture map for disease gene discovery in african americans. *Am J Hum Genet* 74, 1001-13 (2004).
27. Zhu, X. et al. Admixture mapping for hypertension loci with genome-scan markers. *Nat Genet* 37, 177-81 (2005).
28. Romeo, S. et al. Population-based resequencing of ANGPTL4 uncovers variations that reduce triglycerides and increase HDL. *Nat Genet* 39, 513-516 (2007).

The examples and detailed description herein are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for determining a genetic marker in a PNPLA3 gene of a human and treating the human for high hepatic fat content, the method comprising the steps:
   (a) determining that the genome of the human comprises a genetic marker of PNPLA3-I148M by detecting a G allele at SNP rs738409;
   (b) identifying the human as having a high hepatic fat content based on the detection of the G allele at SNP rs738409; and
   (c) treating the human identified in (b) as having a high hepatic fat content with an antiobesity drug that is orlistat, sibutramine, exenatide, pramlintide or rimonabant.

2. The method of claim 1 wherein:
   the determining step comprises detecting the marker using a method selected from the group consisting of: mass spectroscopy, oligonucleotide microarray analysis, allele-specific hybridization, allele-specific PCR, and sequencing, and
   the method further comprises a step of measuring hepatic triglyceride of the human, wherein the measuring step comprises proton magnetic resonance spectroscopy (1H-MRS).

3. The method of claim 1 wherein the drug is orlistat.
4. The method of claim 2 wherein the drug is orlistat.
5. The method of claim 1 wherein the drug is sibutramine.
6. The method of claim 2 wherein the drug is sibutramine.
7. The method of claim 1 wherein the drug is exenatide.
8. The method of claim 2 wherein the drug is exenatide.
9. The method of claim 1 wherein the drug is pramlintide.
10. The method of claim 2 wherein the drug is pramlintide.
11. The method of claim 1 wherein the drug is rimonabant.
12. The method of claim 2 wherein the drug is rimonabant.

13. A method for determining a genetic marker in a PNPLA3 gene of a human and treating the human for high hepatic fat content, the method comprising the steps:
   (a) determining that the genome of the human comprises a genetic marker of PNPLA3-I148M by detecting a G allele at SNP rs738409;
   (b) identifying the human as having a high hepatic fat content based on the detection of the G allele at SNP rs738409; and
   (c) treating the human identified in (b) as having a high hepatic fat content with an anti-diabetic drug that is a thiazolidinedione, metformin or glimepiride.

14. The method of claim 13 wherein:
   the determining step comprises detecting the marker using a method selected from the group consisting of: mass spectroscopy, oligonucleotide microarray analysis, allele-specific hybridization, allele-specific PCR, and sequencing, and
   the method further comprises the step of measuring hepatic triglyceride of the human, wherein the measuring step comprises proton magnetic resonance spectroscopy (1H-MRS).

15. The method of claim 13 wherein the drug is a thiazolidinedione.
16. The method of claim 14 wherein the drug is a thiazolidinedione.
17. The method of claim 13 wherein the drug is metformin.
18. The method of claim 14 wherein the drug is metformin.
19. The method of claim 13 wherein the drug is glimepiride.
20. The method of claim 14 wherein the drug is glimepiride.

* * * * *